US006433214B1

(12) United States Patent
Castaldi et al.

(10) Patent No.: US 6,433,214 B1
(45) Date of Patent: Aug. 13, 2002

(54) PROCESS FOR THE PREPARATION OF 2-(4-METHYLPHENYL)-BENZOIC ACID DERIVATIVES

(75) Inventors: Graziano Castaldi, Briona; Antonio Tarquini, Tortona; Renzo Rossi, Pisa, all of (IT)

(73) Assignee: Dipharma S.p.A., Basiliano (IT)

( * ) Notice: Subject to any disclaimer, the term of this patent is extended or adjusted under 35 U.S.C. 154(b) by 0 days.

(21) Appl. No.: 09/541,951

(22) Filed: Apr. 3, 2000

(30) Foreign Application Priority Data

Apr. 13, 1999 (IT) .......................... MI99A0749

(51) Int. Cl.[7] .............................................. C07C 69/76
(52) U.S. Cl. ....................... 560/102; 558/378; 546/286; 546/311; 549/491; 585/421
(58) Field of Search ........................ 560/102; 558/378; 546/286, 311; 549/491; 585/421

(56) References Cited

FOREIGN PATENT DOCUMENTS

EP 571770 A1 * 12/1993

OTHER PUBLICATIONS

Ueda et al, Tetrahedron , vol. 54, 1998, pp13079–13086.*
Stang et al, Perfluoroalkanesulfonic EstersMethods of Preparation and Applications in Organic Chemistry, Synthesis, 1982, pp. 85 to 126.*
Ueda, et al, Synthesis of Biaryls via Nickel–Catalyzed Cross–Coupling Reaction of Arylboronic Acids and Aryl mesylates, Tetrahedron 54, 1998, pp. 13079–13086.*
Percec et al, Aryl Mesylates in Metal Catalyzed Homo–and Cross–Coupling Reactions, J. Org. Chem. 1995, vol. 60, pp. 6895–6903.*

Ingo Klement et al.: "Preparation of Polyfunctional Aryl and Alkenyl Zinc Halides from Functionalized Unsaturated Organo–lithiums and their Reactivity in Cross–Coupling and Conjugated Addition Reactions" Tetrahedron, vol. 52, No. 21, May 20, 1996, pp. 7201–7220 XP002142341, Elsevier Science Publishers, Amsterdam, NL—ISSN: 0040–4020, p. 7206–p. 7207; table 3 * scheme 7 * p. 7208 * p. 7216, paragraph 2 * p. 7218, paragraph 4—paragraph 5 *.

Virgil Percec et al.: "Aryl Mesylates in Metal–Catalyzed Homo–coupling and Cross–Coupling Reactions. 1.Functional Symmetric Biaryls from Phenols via Nickel–Catalyzed Homocoupling of their Mesylates" Journal of Organic Chemistry, vol. 60, No. 1, Jan. 13, 1995 pp. 176–185, XP002142429 American Chemical Society. Easton., US—ISSN: 0022–3263 * p. 183, right–hand col., paragraph 5—p. 185, left–hand col., paragraph 8.

G.W. Kenner et al.: "The Cleavage of Sulphonic Esters with Raney Nickel Catalysts" Journal of the Chemical Society, 1949, pp. s178–s181, XP002142430—Chemical Society, Letchworth, GB * Experimental * p. S179 *.

* cited by examiner

Primary Examiner—Paul J. Killos
Assistant Examiner—Hector Reyes

(57) ABSTRACT

A process for the preparation of 2-(4-methylphenyl)benzoic acid $C_{1-6}$alkyl esters by reaction of a sulfonic derivative of formula

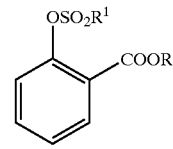

wherein R is $C_{1-6}$alkyl and $R^1$ is optionally perfluorinated $C_{1-6}$alkyl or optionally substituted $C_{1-6}$aryl, with a 4-methylphenylzinc halide.

7 Claims, No Drawings

PROCESS FOR THE PREPARATION OF 2-(4-METHYLPHENYL)-BENZOIC ACID DERIVATIVES

The present invention relates to the organic chemistry field.

More particularly, the invention relates to a process for the preparation of 2-(4-methylphenyl)benzoic acid esters.

2-(4-Methylphenyl)benzoic acid is a useful intermediate for the synthesis of 2-(4-methylphenyl)-benzonitrile, also known under the name OTBN (ortho-toluylbenzonitrile), and/or of the corresponding tetrazolyl derivative MBT, which, as it is illustrated in the following Scheme 1, are in their turn key intermediates in the synthesis of "Sartans", which are angiotensin II antagonistic compounds used as antihypertensives.

SCHEME 1

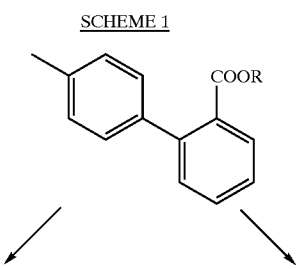

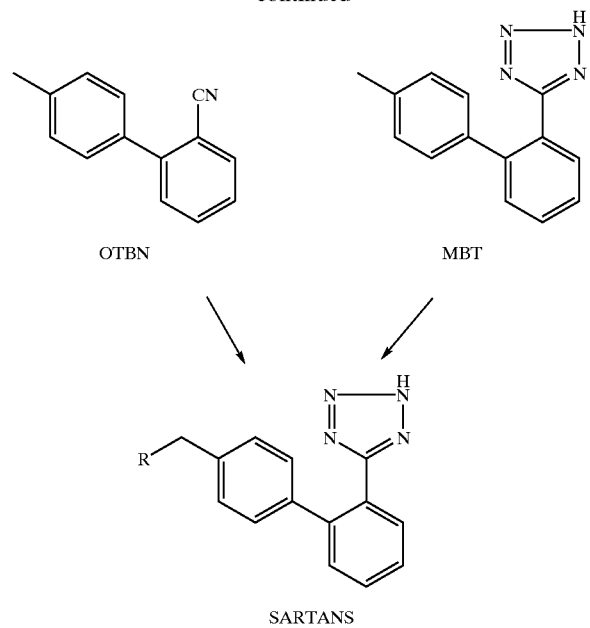

A number of methods for the preparation of OTBN are available, as reported in Chemistry Today, 1998, March/April, 18 and in Specialty Chem., 1998, 436, and as summarized in Scheme 2.

SCHEME 2

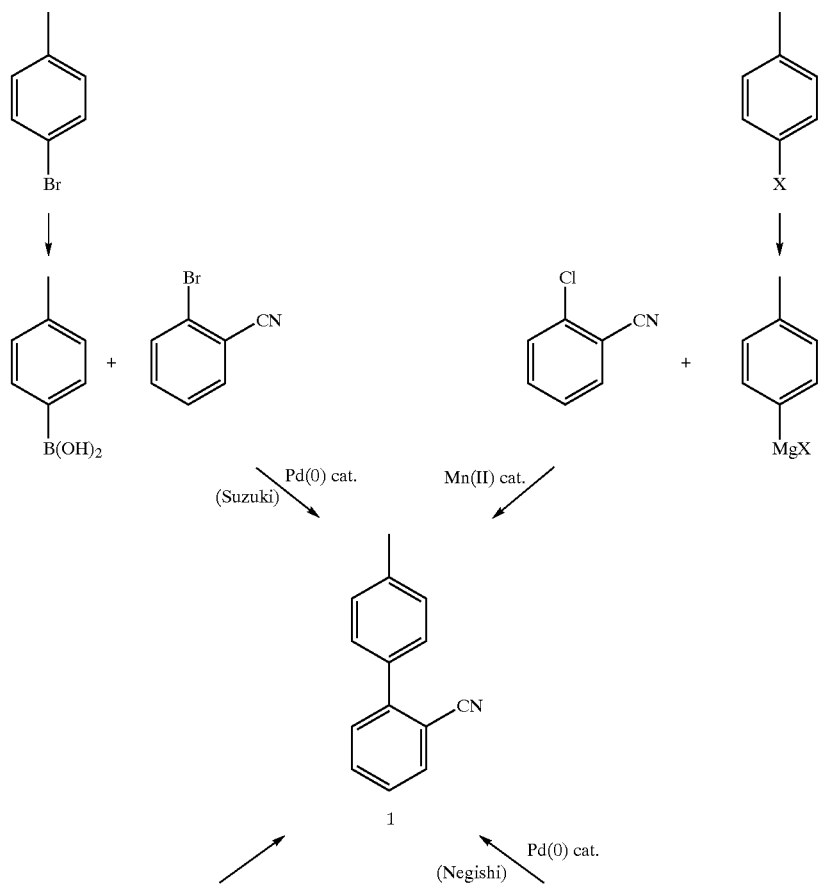

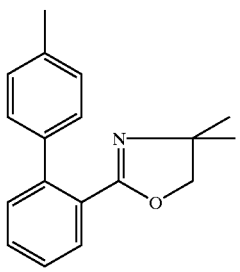

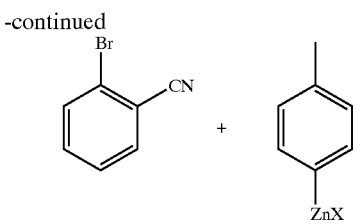

(Meyers) ↑

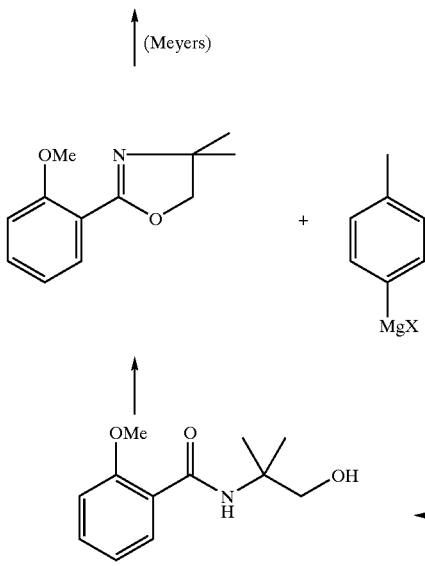

Said methods are described in Angew. Chem.Int.Ed.Engl., 1995, 34, 1844; J.Org.Chem., 1999, 64, 10; Tetrahedron Lett. 1998, 39, 6441; Tetrahedron Lett., 1999, 40, 197.

The syntheses according to Suzuki and Negishi (Scheme 2), though efficient, start from 2-bromobenzonitrile, a very expensive commercial reagent. On the other hand, the synthesis according to Meyers starts from less costly 2-methoxybenzoic acid, but it involves a high number of chemical steps. Recent works exist (see the above cited documents) concerning the preparation of OTBN, through cross-coupling organometal reactions between 4-methylphenyl-metal derivatives and the less expensive 2-chlorobenzonitrile catalyzed by palladium (0) and nickel (0).

Particularly interesting is the Clariant process for the synthesis of OTBN starting from 2-chlorobenzonitrile and 4-methylphenylboronic acid by means of the Suzuki reaction reported in Scheme 3.

SCHEME 3

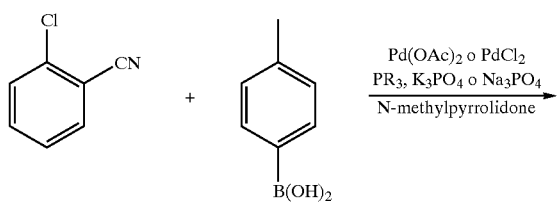

Alternatively to the direct preparation of OTBN starting from benzonitrile precursors, a cross-coupling reaction starting from the corresponding benzoic esters has also been studied.

For example, the reaction of 4-bromotoluene and methyl 2-chlorobenzoate in the presence of NiCl$_2$, PPh$_3$ and zinc powder in pyridine at 80° C. yields the corresponding biphenyl derivatives with low selectivity. (Scheme 4) (Synlett, 1994, 371).

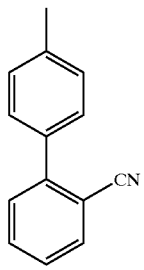

Scheme 4

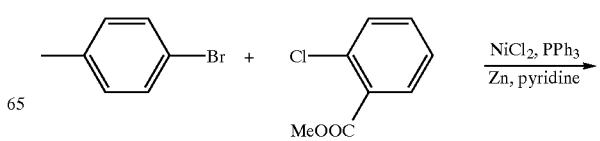

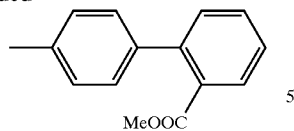

Methyl 2-(4-methylphenyl)-benzoate has recently been obtained in a 47% yield, i.e. with low selectivity, by the Ni-mediated cross-coupling reaction between 4-methylphenylboronic acid and methyl 2-methanesulfonyloxybenzoate (Scheme 5) (Tetrahedron, 1998, 54, 13079).

Scheme 5

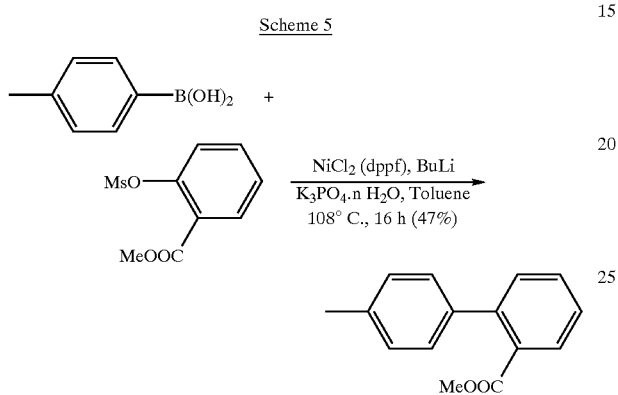

Methyl 2-methanesulfonyloxybenzoate is easily prepared starting from methyl salicylate, a derivative available in large amounts at very low costs. However, the low selectivity of the cross-coupling reaction with 4-methoxyphenylboronic acid does not advantageously yields the bi-phenyl derivative.

Generally speaking, the cross-coupling reactions between an arylsulfonate and organozinc derivatives catalyzed by nickel (0) are known to result in low selectivity (Scheme 6) (J.Org.Chem. 1995, 60, 6895).

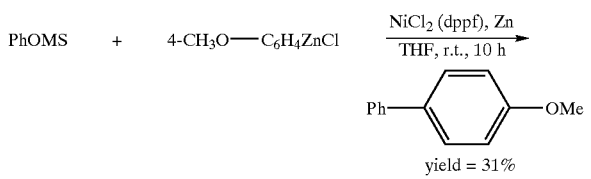

The present invention aims at providing a process for the preparation of 2-(4-methylphenyl)benzoic acid esters in good yields starting from inexpensive starting materials.

Therefore, the invention provides a process for the preparation of 2-(4-methylphenyl)benzoic acid esters of formula (I)

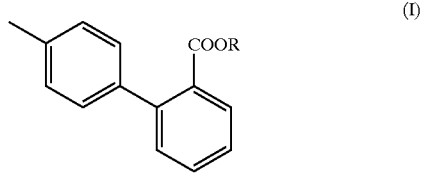

(I)

wherein R is $C_{1-6}$alkyl, comprising the reaction of a sulfonic derivative of formula (II)

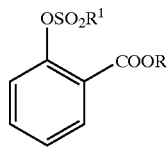

(II)

wherein R is as defined above and $R^1$ is selected from the group consisting of optionally perfluorinated $C_{1-6}$alkyl and optionally substituted $C_{6-10}$aryl, with an arylzinc compound of formula (III)

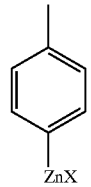

(III)

wherein X is a halogen selected from chlorine, bromine and iodine, in an organic solvent and in the presence of a catalyst based on palladium (0) or nickel (0).

The catalyst is preferably selected from the group consisting of elementary Pd or Ni (metal, cluster etc.) optionally supported (for example on charcoal), Pd or Ni complexes with ligands both preformed and generated in situ by reduction of Pd(II) or Ni(II) salts in the presence of ligands. The latter are preferably selected from the group consisting of phosphorous (III) derivatives, such as triphenylphosphine, tritolylphosphine, tributylphosphine, 1,2-bis-diphenylphosphinoethane and bis-diphenylphosphino-ferrocene. The reduction can be carried out using, for example, magnesium, zinc, alkyllithium, in particular n-butyllithium, triethylamine, triphenylphosphine and the like.

Examples of suitable Pd and Ni salts are Pd acetate, Pd chloride, Ni acetate, Ni chloride.

Examples of Pd and Ni complexes are bis-(triphenylphosphino)-dichloro; bis-(tributylphosphino)-dichloro; tetrakis-(triphenylphosphine); triphenylphosphino-piperidine-dichloro; bis-(triphenylphosphine)-diacetate; 1,2-bis-(diphenylphosphino)-ethane complexes.

The substituent $R_1$ is preferably selected from the group consisting of perfluoroethyl, perfluorobutyl, perfluoroctyl, 4-methylphenyl, 4-nitrophenyl, 2-naphthyl and 1-naphthyl.

The organic solvent used in the reaction is preferably selected from the group consisting of aromatic hydrocarbons, in particular toluene and xylene, and aliphatic ethers, particularly methyl tert-butyl ether, or alicyclic hydrocarbons, in particular tetrahydrofuran, and mixtures thereof. The solvent is used in amounts ranging between 1 and 10 volumes, preferably between 2 and 5 volumes, compared with the compound of formula (II).

The reaction is generally carried out at temperatures ranging from 0° to 150° C., preferably from 20 to 80° C., using 1 to 2, preferably 1.2 to 1.5, equivalents of arylzinc of formula (III) per equivalent of sulfonic derivative of formula (II).

The molar amount of Pd(0) or Ni(0) used compared with the sulfonic derivative of formula (II) ranges from 0.01 to 0.05 and is preferably 0.02.

The compound of formula (I) is generally obtained in yields >70% after filtration from the reaction mixture, addition of water, separation of the phases, evaporation of the solvent from the organic phase and drying. A further purification by crystallization or by silica gel chromatography can be carried out, if necessary.

Alternatively, the resulting compound can be saponified to give the corresponding 2-(4-methylphenyl)-benzoic acid.

The arylzinc compounds of formula (III) can be prepared, according to known techniques, starting from the corresponding aryl halides.

The sulfonic derivative of formula (II) is in its turn prepared by reaction of an alkyl salicylate of formula (IV)

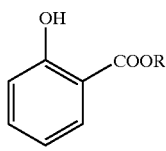

(IV)

wherein R is $C_{1-6}$alkyl, with a sulfonyl chloride of formula $R^1SO_2Cl$, in which $R^1$ is as defined for compounds of formula (II), in an organic solvent and in the presence of a base.

The organic solvent used for said reaction is selected from the group consisting of optionally chlorinated aromatic hydrocarbons, $C_{1-4}$alkyl acetates, $C_{1-4}$ haloalkanes and aliphatic and alicyclic $C_{1-6}$ketones, and mixtures thereof. Said solvent is used in amounts ranging from 1 to 10 volumes, preferably from 2 to 5 volumes, compared with compound (IV). Examples of suitable solvents are toluene, xylene, ethyl acetate, butyl acetate, acetone, methyl ethyl ketone, cyclohexanone, chlorobenzene and methylene chloride.

The reaction is usually carried out at temperatures ranging from −20° to 50° C., preferably from 0° to 30° C., using 1 to 2 equivalents of $R^1SO_2Cl$ and 1 to 2, preferably 1.2 to 1.5, equivalents of base per equivalent of alkyil salicylate of formula (IV).

The base used in the above reaction is selected from the group consisting of oxides, hydroxides, carbonates and bicarbonates of alkali metals, such as sodium, potassium, lithium, and tertiary amines, such as triethylamine, diisopropylethylamine, N-methylmorpholine, diazabicycloctane.

The sulfonic derivative of formula (II) is generally obtained in yields >80% by addition of water to the reaction mixture, separation of the phases, evaporation of the organic phase and drying. The derivative of formula (II) can be purified, if necessary, by crystallization from solvents such as n-hexane, n-heptane, ligroine, methanol, ethanol, isopropanol, n-butanol, and the like.

The synthetic strategy selected for the process according to the present invention consisted in starting from inexpensive raw materials, commercially available in large amounts and providing the formation of the biphenyl derivative through a reaction catalyzed by organometal complexes. The least expensive, commercially available benzoic derivative functionalized at the 2 position is salicylic acid and the esters thereof.

The yield and the selectivity obtained by reacting a salicylic acid sulfonic derivative with an arylzinc compound are surprisingly high in view of what reported in the prior art.

The characteristics and advantages of the process of the invention will be further evidenced by the following non limiting examples.

EXAMPLE 1

Preparation of p-tolylzinc Bromide

A mixture of metal magnesium (1.5 g, 60 mmoles) and dry tetrahydrofuran (30 ml), refluxed under inert atmosphere (nitrogen), is added with a solution of p-bromotoluene (10.8 g, 65 mmoles) in dry tetrahydrofuran (20 ml). After 1 hour, a solution of dry zinc chloride (11.4 g, 83 mmoles) in dry tetrahydrofuran (60 ml) is added keeping stirring for 1 hour until p-tolylzinc bromide precipitates. The resulting suspension can be used in the subsequent step.

EXAMPLE 2

Preparation of methyl 2-[1-(perfluorobutane) sulfonyloxy]benzoate

A mixture of methyl salicylate (50 g; 328 mmoles), 1-(perfluorobutane) sulfonyl fluoride (149 g; 493 mmoles) and acetonitrile (800 ml), under inert atmosphere (nitrogen), is added in about 20' with triethylamine (50 g; 493 mmoles). The mass is heated to 40÷45° C. keeping this temperature until completion of the reaction (12 hours), the solvent is evaporated off under vacuum to a residue, which is taken up with 400 ml of a water-toluene 50:50 mixture. The phases are separated: the organic phase is washed twice with 100 ml of water whereas the aqueous phase is extracted with 100 ml of toluene. The combined organic phases are dried over sodium sulfate and evaporated under vacuum to a residue, to obtain methyl 2-[1-(perfluorobutane)sulfonyloxy]benzoate (140 g, 97% purity, 98% yield).

$^1$H NMR (DMSO, δ in ppm) : 3.88 (s, 3H) , 7.53–8.08 (m, 4H)

EXAMPLE 3

Preparation of methyl 2-(methanesulfonyloxy) benzoate

A solution of methyl salicylate (200 g, 1310 mmoles) and methanesulfonyl chloride (210 g, 1830 mmoles) in toluene (600 ml), cooled at 5÷10° C. and under inert atmosphere (nitrogen), is slowly added (about 1 hour) with triethylamine (192 g, 1900 mmoles). The mixture is stirred for 20 hours, then poured into water (1500 ml) and the phases are separated. The aqueous phase is extracted twice with 250 ml of toluene. The combined organic phases are washed twice with 250 ml of water, dried over sodium sulfate, then evaporated under vacuum to a residue which is recrystallized from isopropanol (590 ml) to yield methyl 2-(methanesulfonyloxy)benzoate (280 g, 99.8% purity, 89% yield).

$^1$H NMR (CDCl$_3$, δ in ppm) 2.94 (s, 3H), 3.59 (s, 3H); 7.02–7.66 (m, aromatic, 4H).

Mass-EI m/e (%): 230 (M$^+$), 199, 152, 135, 120. 92.

EXAMPLE 4

Preparation of methyl 2-(4-methylphenyl)benzoate

A mixture of palladium trisdibenzylideneacetone (0.35 g, 3.9 mmoles), diphenylphosphinoferrocene (0.21 g, 3.9 mmoles) and dry tetrahydrofuran (25 ml) is heated under inert atmosphere to an inner temperature of 40° C. After 30', methyl 2-[1-(perfluorobutane)sulfonyloxy]benzoate (15.3 g, 35 mmoles, prepared as described in Example 2), is added at 40° C. After 1 hour this mixture is added to a suspension of p-tolylzinc bromide prepared as described in Example 1. The resulting mixture is refluxed until completion of the reaction (12 hours), cooled to 25° C., then poured into a solution of water (100 ml) and 37% hydrochloric acid (25 ml). The phases are separated, the organic phase is shaken with a water-dichloromethane mixture; the phases are separated again and the organic one is evaporated under vacuum to a residue, to obtain methyl 2-(4-methylphenyl)benzoate as an oil (4 g, 50% yield).

$^1$HNMR (DMSO, δ in ppm): 2,34(s, 3H); 3.59(s, 3H); 7,19–7.75(m, aromatic, 8H).

Mass-EI m/e (%): 226 (M+), 212,195, 165, 152, 139.

EXAMPLE 5

Preparation of methyl 2-(4-methylphenyl)benzoate

A mixture of 10% Pd—C (0.89 g, 0.84 mmoles), triphenylphosphine (0.43 g, 1.7 mmoles) and dry tetrahydrofuran (25 ml) is heated under inert atmosphere to 40° C. inner temperature. After 30', methyl 2-[1-(perfluorobutane)sulfonyloxy]benzoate (19.1 g, 44 mmoles, prepared as described in Example 2) is added at 40° C. After 1 hour this mixture is added to a suspension of p-tolylzinc bromide prepared as described in Example 1. The resulting mixture is refluxed until completion of the reaction (23 hours), cooled to 25° C. then poured into a solution of water (100 ml) and glacial acetic acid (6 g). The phases are separated, the organic phase is extracted with a water-dichloromethane mixture (70 ml; 50:50); the phases are separated again and the organic one is evaporated under vacuum to a residue, to obtain methyl 2-(4-methylphenyl)benzoate as an oil (5 g, yield 50%).

EXAMPLE 6

Preparation of methyl 2-(4-methylphenyl)benzoate

A mixture of palladium chloride (0.15 g, 0.84 mmoles), triphenylphosphine (0.55 g, 2.1 mmoles) and dry tetrahydrofuran (25 ml) is refluxed under inert atmosphere (67° C.). After 90', methyl 2-[1-(perfluorobutane)sulfonyloxy]benzoate (19.1 g, 44 mmoles, prepared as described in Example 2) is added. After 1 hour this mixture is added to a suspension of p-tolylzinc bromide prepared as described in Example 1. The resulting mixture is refluxed until completion of the reaction (72 hours), cooled to 25° C. then poured into a solution of water (100 ml) and 37% hydrochloric acid (25 ml). The phases are separated, the organic phase is extracted with a water-dichloromethane mixture (70 ml; 50:50); the phases are separated again and the organic one is evaporated under vacuum to a residue, to obtain methyl 2-(4-methylphenyl)benzoate as an oil (7.8 g, yield 79%).

EXAMPLE 7

Preparation of methyl 2-(4-methylphenyl)benzoate

A mixture of nickel chloride (0.11 g, 0.85 mmoles), triphenylphosphine (0.44 g, 1.7 mmoles), and dry tetrahydrofuran (25 ml), at room temperature and under inert atmosphere (nitrogen), is added with 1.6 M n-butyllithium (1.1 ml; 1.7 mmoles); the mixture is kept under stirring for 15', then added with methyl 2-(methanesulfonyloxy)benzoate (10.1 g, 44 mmoles, prepared as described in Example 3) dissolved in dry tetrahydrofuran (10 ml). After further 15' under stirring, the resulting mixture is added to a suspension of p-tolylzinc bromide prepared as described in Example 1, previously added with lithium chloride (2.3 g, 54 mmoles). The resulting mixture is kept at room temperature for 12 hours, then poured into a solution of water (100 ml) and 37% hydrochloric acid (25 ml); the phases are separated, the organic phase is extracted with a water-dichloromethane mixture (50 ml; 50:50); the phases are separated again and the organic one is dried over sodium sulfate and evaporated under vacuum to a residue, to obtain methyl 2-(4-methylphenyl)benzoate as an oil (8.2 g, yield 82%).

EXAMPLE 8

Preparation of methyl 2-(4-methylphenyl)benzoate

A mixture of nickel chloride (0.11 g, 0.85 mmoles), triphenylphosphine (0.44 g, 1.7 mmoles), and dry tetrahydrofuran (25 ml), at room temperature and under inert atmosphere (nitrogen), is added with 1.6 M n-butyllithium (1.1 ml; 1.7 mmoles); the mixture is kept under stirring for 15', then added with methyl 2-[1-(perfluorobutane)sulfonyloxy]benzoate (19.1 g, 44 mmoles, prepared as described in Example 2) dissolved in dry tetrahydrofuran (10 ml). After further 15' under stirring, the resulting mixture is added to a suspension of p-tolylzinc bromide prepared as described in Example 1, previously added with lithium chloride (2.3 g, 54 mmoles). The resulting mixture is kept at room temperature for 12 hours, then poured into a solution of water (100 ml) and 37% hydrochloric acid (25 ml); the phases are separated, the organic phase is extracted with a water-dichloromethane mixture (50 ml; 50:50); the phases are separated again and the organic one is dried over sodium sulfate and evaporated under vacuum to a residue, to obtain methyl 2-(4-methylphenyl)benzoate as an oil (9 g, yield 91%).

What is claimed is:

1. A process for the preparation of 2-(4-methylphenyl)benzoic acid esters of formula (I)

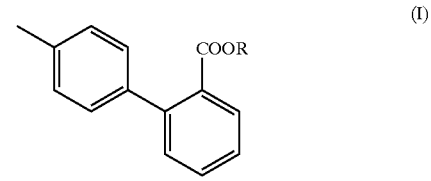

(I)

wherein R is $C_{1-6}$alkyl, which comprises reacting a sulfonic derivative of formula (II)

(II)

wherein R is as defined above and $R^1$ is a member selected from the group consisting of an unsubstituted $C_{1-6}$alkyl or perfluorinated $C_{1-6}$alkyl, and unsubstituted $C_{6-10}$aryl or perfluorinated $C_6$–$C_{10}$aryl, with an arylzinc compound of formula (III)

(III)

wherein X is a halogen which is a member selected from the group consisting of chlorine, bromine and iodine, in an organic solvent and in the presence of a catalyst based on palladium (0) or nickel (0).

2. The process as claimed in claim 1 wherein said organic solvent is a member selected from the group consisting of aromatic hydrocarbons, aliphatic ethers, alicyclic hydrocarbons and mixtures thereof.

3. The process as claimed in claim 2 wherein the aromatic hydrocarbon is toluene or xylene, the aliphatic ether is methyl tert-butyl ether, and the alicyclic hydrocarbon is tetrahydrofuran.

4. The process as claimed in claim 1 wherein the reaction is carried out at a temperature of 0° up to 150° C., using 1 to 2 equivalents of said arylzinc of formula (III) per equivalent of sulfonic derivative of formula (II).

5. The process as claimed in claim 3 wherein the molar amount of Pd(0) or Ni(0) compared with the sulfonic derivative of formula (II) ranges from 0.01 to 0.05.

6. The process as claimed in claim 1 wherein said catalyst is a member selected from the group consisting of unsupported or supported elementary Pd or Ni, complexes of Pd or Ni with a ligand both preformed and generated in situ by reduction of Pd(II) or Ni(II) salts, said ligand being a phosphorous (III) derivative which is a member selected from the group consisting of triphenylphosphine, tritolylphosphine, tributylphosphine, 1,2-bis-diphenylphosphinoethane, bis-diphenylphosphinoferrocene.

7. The process according to claim 1 wherein $R^1$ is a member selected from the group consisting of perfluoroethyl, perfluorobutyl, perfluoroctyl, 4-methylphenyl, 4-nitrophenyl, 2-naphthyl and 1-naphthyl.

* * * * *